United States Patent
Abdallah et al.

(10) Patent No.: US 11,998,582 B1
(45) Date of Patent: Jun. 4, 2024

(54) COMPOSITION FOR TREATING BONE LOSS

(71) Applicant: KING FAISAL UNIVERSITY, Al-Ahsa (SA)

(72) Inventors: Basem Mohamed Abdallah, Hofouf (SA); Enas Mohamed Ali, Hofouf (SA)

(73) Assignee: KING FAISAL UNIVERSITY, Al Hasa (SA)

( * ) Notice: Subject to any disclaimer, the term of this patent is extended or adjusted under 35 U.S.C. 154(b) by 0 days.

(21) Appl. No.: 18/529,504

(22) Filed: Dec. 5, 2023

(51) Int. Cl.
 *A61K 36/00* (2006.01)
 *A61K 36/53* (2006.01)
 *A61P 19/10* (2006.01)

(52) U.S. Cl.
 CPC .............. *A61K 36/53* (2013.01); *A61P 19/10* (2018.01); *A61K 2236/15* (2013.01); *A61K 2236/17* (2013.01); *A61K 2236/31* (2013.01); *A61K 2236/33* (2013.01)

(58) Field of Classification Search
 CPC .................................................... A61K 36/53
 See application file for complete search history.

(56) References Cited

FOREIGN PATENT DOCUMENTS

| CN | 111991542 A | 11/2020 |
| CN | 115282188 A | 11/2022 |
| JP | 2020015709 A | * 1/2020 |

OTHER PUBLICATIONS

Guelcin et al, Comparison of antioxidant activity of clove (*Eugenia caryophylata* Thunb) buds and lavender (*Lavandula stoechas* L.). Food Chemistry (2004), vol. 87, No. 3, pp. 393-400 (Year: 2004).*

Abdolreza Abri and Monireh Noroozi Extraction and identification of Gallic acid and some active ingredients in Lavandula angustifolia plant and synthesis of silver nanoparticles by green method from the extract of this plant, DOI:10.22075/CHEM.2021.20160.1824.

Zhizhong Zhang, Yu Zheng, Lipeng Zhang, Mohan Prasath Mani and Saravana Kumar In vitro blood compatibility and bone mineralization aspects of polymeric scaffold laden with essential oil and metallic particles for bone tissue engineering, DOI.org/10.1080/1023666X.2019.1611029.

Mohammad Hossein Abnosi, Javad Sargolzaei, and Farshid Nazari, Gallic Acid Ameliorates Cadmium Effect on Osteogenesis by Activation of Alkaline Phosphatase and Collagen Synthesis. DOI:10.22074/CELLJ.2023.1999.110.1263.

Manohar Shirugumbi Hanamanthagouda, Siddappa Bhimashya Kakkalameli, Poornananda Madhava Naik, Praveen Nagella, Harisha Reddy Seetharamareddy, & Hosakatte Niranjana Murthy Essential oils of Lavandula bipinnata and their antimicrobial activities, doi.org/10.1016/j.foodchem.2009.05.032.

* cited by examiner

Primary Examiner — Qiuwen Mi
(74) Attorney, Agent, or Firm — Nath, Goldberg & Meyer; Richard C. Litman

(57) ABSTRACT

The composition for treating bone loss is an alcoholic extract of *Lavandula atriplicifolia* plant flowers and leaves. The composition is prepared by extracting dried *Lavandula* plant flower and leaf powder in ethanol or methanol for at least 4 hours in a Soxhlet apparatus. The *Lavandula atriplicifolia* extract acts by both stimulating osteogenesis and inhibiting adipogenesis. The composition may be used to form drug compositions for treating bone loss.

9 Claims, 2 Drawing Sheets

COMPOSITION FOR TREATING BONE LOSS

BACKGROUND

1. Field

The disclosure of the present patent application relates to treating bone loss, and particularly to a composition for treating bone loss that includes an alcoholic extract of *Lavandula atriplicifolia*.

2. Description of the Related Art

Osteoporosis is a systemic bone loss-related disease characterized by reduced bone mass due to increased bone resorption by osteoclast cells on the expenses of bone formation by osteoblast cells. The bone-forming progenitor osteoblast cells are derived from adult stem cells in bone marrow. Most drug therapy for osteoporosis is based mainly on inhibiting bone resorption (anti-catabolics), rather than enhancing bone formation. Thus, there is a need to develop new drug approach for targeting the stimulation of bone formation.

*Lavandula* is a genus of flowering plants in the mint family native to Europe, Africa, and southwest Asia. The genus includes 47 known species, including *L. angustifolia, L. dentata, L. atriplicifolia*, etc. that are known to contain a variety of phytochemicals and other useful compounds found to be useful in folk and natural medicines for treatment of various conditions, including insomnia, intestinal discomfort, and cardiovascular diseases.

Thus, a composition for treating bone loss solving the aforementioned problems is desired.

SUMMARY

The present subject matter relates to a composition for treating bone loss comprising an alcoholic extract of *Lavandula atriplicifolia* flowers and leaves. The composition is prepared by crushing *Lavandula* flowers and leaves to obtain a fine powder and extracting the powdered *Lavandula* in ethanol and methanol for 4 hours at room temperature, for example, in a Soxhlet apparatus. The resulting *Lavandula* extract may be used to both stimulate osteogenesis and to inhibit adipogenesis. The *Lavandula* extract may be used to form drug compositions for treating bone loss.

These and other features of the present subject matter will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
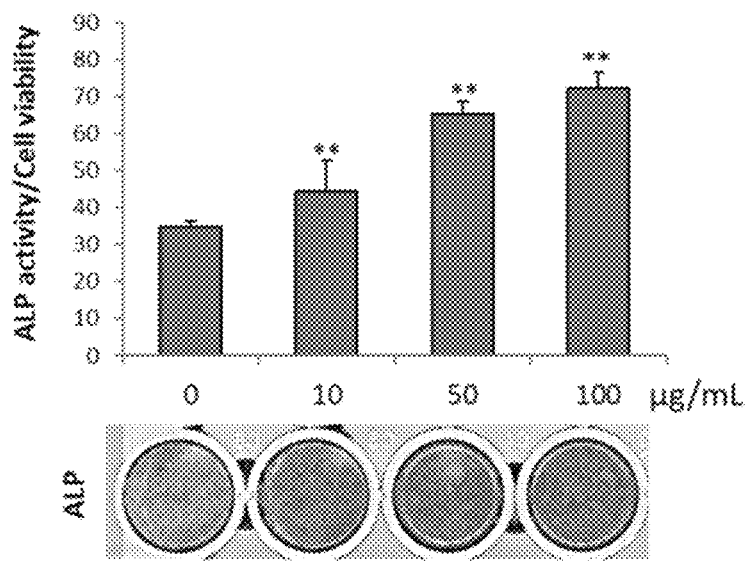
FIG. 1A is a graph showing the dose dependent stimulatory effect of *Lavandula atriplicifolia* on osteoblast differentiation of BMSCs as measured by quantitative alkaline phosphatase activity (ALP) after 6 days of osteogenic induction. All values are mean+SD of three independent experiments (*$p<0.05$, **$p<0.005$, compared to non-treated cells)

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as bone loss or osteoporosis.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The composition for treating bone loss as described herein can be formed as an alcoholic extract of *Lavandula atriplicifolia* flowers and leaves. The composition can be prepared by crushing *Lavandula* flowers and leaves to obtain a fine powder and extracting the powdered *Lavandula* in ethanol and methanol for about 4 hours at room temperature, for example, in a Soxhlet apparatus. The resulting *Lavandula* extract may be used to both stimulate osteogenesis and to inhibit adipogenesis. The *Lavandula* extract may be used to form drug compositions for treating bone loss.

In certain embodiments of the composition as described herein, the extract of a *Lavandula atriplicifolia* plant can comprise vanillic acid, gallic acid, and hydroxycinnamic acid. In other embodiments, the composition as described herein can further comprise a mixture of phenolic compounds.

In an embodiment, the present compositions for treating bone loss can be formulated as an oral composition.

In this regard, the present subject matter is further directed to pharmaceutical compositions comprising a therapeutically effective amount of the composition as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises a present composition together with at least one pharmaceutically acceptable auxiliary.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

The present composition is typically administered at a therapeutically or pharmaceutically effective dosage, e.g., a dosage sufficient to provide treatment for osteoporosis or bone loss. Administration of the compound or pharmaceutical compositions thereof can be by any method that delivers the compound systemically and/or locally. These methods include oral routes and the like.

While human dosage levels have yet to be optimized for the present composition, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present composition for treatment of osteoporosis or bone loss, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols, or the like. The present compositions can also be administered in sustained or controlled release dosage forms, including osmotic pumps, pills, and the like, for the prolonged administration of the compound at a predetermined rate, preferably in unit dosage forms suitable for single administration of precise dosages.

The present compositions may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of the present composition, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscarmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum, and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

The composition for treating bone loss will be explained in the following examples. Materials and test methods in the examples include the following.

Primary mouse bone marrow derived-mesenchymal stem cells (BMSCs) were cultured at 15,000 cells/cm$^2$ in CIM medium. At 70% cell confluence, cultured media were changed to osteogenic-induction medium (OIM), which included: α-minimum essential medium (α-MEM) containing 10% FBS, 100 U/mL of penicillin, 100 mg/mL of streptomycin, 50 µg/mL of vitamin C (Sigma-Aldrich), 10 nM dexamethasone and 10 mM β-glycerol-phosphate.

Adult adipose-derived stem cells were cultured at 15,000 cells/cm$^2$ in CIM medium. At 100% cell confluence, cultured media were replaced by adipogenic-induction medium (AIM), which included: DMEM supplemented with 9% horse serum, 450 µM 1-methyl-3-isobutylxanthine (IBMX), 250 nM dexamethasone. Cells were cultured in AIM for 12 days (or as indicated). The media were changed every 2-3 days during the time course of adipocyte differentiation.

Example 1

Preparation of *Lavandula* Plant Extract

Fresh flowers and leaves of *Lavandula atriplicifolia* were washed thoroughly with running water and with sterile distilled water. The washed fresh plant materials were air dried, and then the dried materials were crushed into fine powder using a blender. The powdered flowers and leaves of the plant samples (40 g) were extracted with either ethanol or methanol (250 mg/mL) using a Soxhlet apparatus. Extraction was conducted for 4 hours. All of the solvents were evaporated and then the resulting extracts were dissolved in their solvent at a concentration between 100-200 mg/mL and then kept in small sterile opac bottles under refrigerated conditions until used.

Example 2

Effect of *Lavandula* Plant Extract on Osteoblast Differentiation of BMSCs

BMSCs were cultured at 15,000 cells/cm$^2$ in CIM medium. At 70% cell confluence, cultured media were changed to osteogenic-induction medium (OIM) including: α-minimum essential medium (α-MEM) containing 10% FBS, 100 U/mL of penicillin, 100 mg/ml of streptomycin, 50 µg/mL of vitamin C (Sigma-Aldrich), 10 nM dexamethasone and 10 mM β-glycerol-phosphate.

Figure 1B:
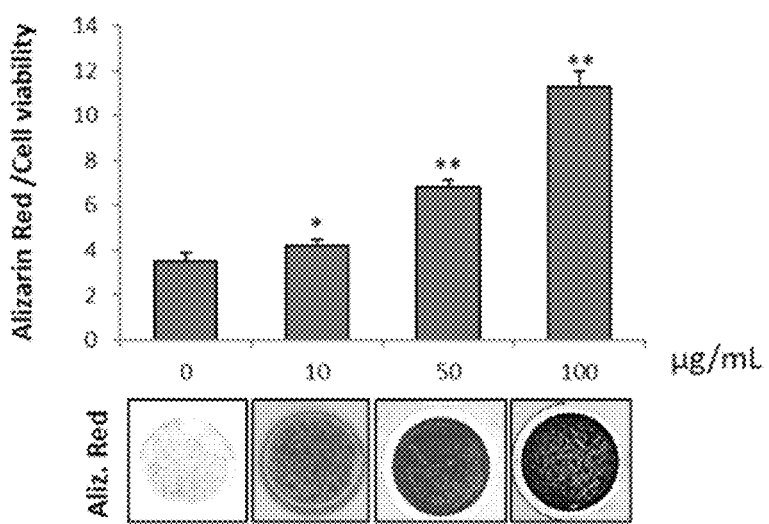
FIG. 1B is a graph showing the dose dependent stimulatory effect of *Lavandula atriplicifolia* on osteoblast differentiation of BMSCs as measured by Alzarin red staining after 12 days of osteogenic induction. All values are mean+SD of three independent experiments (*$p<0.05$, **$p<0.005$, compared to non-treated cells)

BMSCs were induced to differentiate into osteoblasts as mentioned above in the absence or the presence of different concentrations of *Lavandula atriplicifolia* extract, for 12 days. As shown in FIGS. 1A-1B, *Lavandula atriplicifolia* extract stimulated in dose-dependent manner the differentiation of BMSCs cells into osteoblast lineage, as measured by increasing the alkaline phosphatase activity and matrix mineralization using Alizarin red staining.

Example 3

Effect of *Lavandula* Plant Extract on Adipocyte Differentiation of Adipose-Derived Stem Cells Adult adipose-derived stem cells were cultured at 15,000 cells/cm$^2$ in CIM medium. At 100% cell confluence, cultured media were replaced by adipogenic-induction medium (AIM) including: DMEM supplemented with 9% horse serum, 450 µM 1-methyl-3-isobutylxanthine (IBMX), 250 nM dexamethasone. Cells were cultured in AIM for 12 days (or as indicated). The media were changed every 2-3 days during the time course of adipocyte differentiation.

BMSCs cells were induced to adipocyte differentiation as mentioned above without or with different concentrations of plant extract of *Lavandula atriplicifolia* for 12 days.

Figure 2:
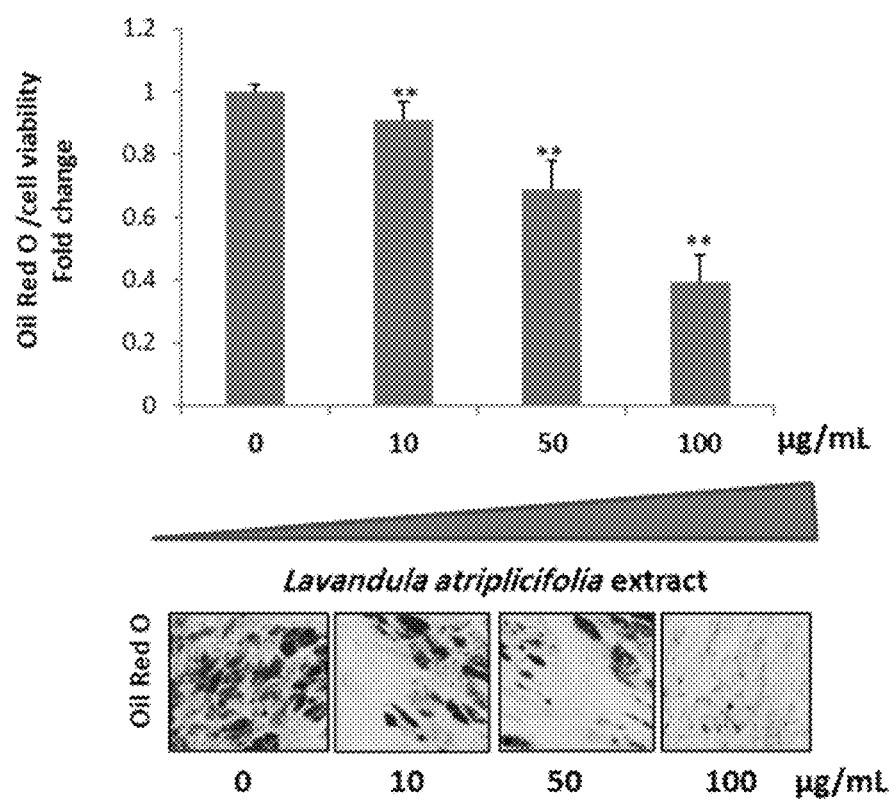
FIG. 2 is a graph showing the dose dependent inhibitory effect of *Lavandula atriplicifolia* extract (10-100 µg/ml) on adipocyte differentiation of stem cells as measured by Oil red O quantification of lipid accumulation. All values are mean+SD of three independent experiments (*$p<0.05$, **$p<0.005$, compared to 0 Conc.)

As shown in FIG. 2, a dose-dependent inhibitory effect of *Lavandula atriplicifolia* extract on adipocyte formation by stem cells was identified by reduction in the quantification of Oil-red O staining for lipid accumulation by the cells.

The above-described composition for treating bone loss may be used as a pharmaceutical, or used to develop a pharmaceutical, as an emulsion or in liquid or powder form, with or without the addition of excipients, such as binders and fillers, and may be formulated as a capsule or tablet for oral administration or may be administered intravenously by injection or infusion. It is anticipated that the dosage may be determined without undue experimentation and adjusted as needed by routine monitoring, such as testing bone density, to treat and counteract bone porosity in osteoporosis and similar conditions.

It is to be understood that the composition for treating bone loss is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A composition for treating bone loss, comprising an extract of a *Lavandula atriplicifolia* plant and an orally acceptable carrier selected from the group consisting of a tablet, a capsule, a powder, and a suspension, wherein the extract of the *Lavandula atriplicifolia* plant is obtained by a method comprising:
   providing fresh flowers and leaves of the *Lavandula atriplicifolia* plant;
   drying the fresh flowers and leaves of the *Lavandula atriplicifolia* plant to obtain dried plant materials;
   crushing the dried plant materials to obtain a plant powder; and
   extracting the plant powder in a solvent using a Soxhlet apparatus to obtain a resulting extract.

2. The composition for treating bone loss according to claim 1, wherein the extract of a *Lavandula atriplicifolia* plant is an extract in ethanol as an extraction solvent.

3. The composition for treating bone loss according to claim 1, wherein the extract of a *Lavandula atriplicifolia* plant is an extract in methanol as an extraction solvent.

4. The composition for treating bone loss according to claim 1, wherein the extract of a *Lavandula atriplicifolia* plant comprises vanillic acid, gallic acid, and hydroxycinnamic acid.

5. The composition for treating bone loss according to claim 1, further comprising a mixture of phenolic compounds.

6. A method for treating bone loss, comprising the step of administering to a patient in need thereof an effective amount of the composition of claim 1 for reducing bone loss.

7. The method of claim 6, further comprising stimulating differentiation of cells into osteoblasts in the patient.

8. The method of claim 6, further comprising inhibiting differentiation of cells into adipocytes in the patient.

9. The method of claim 6, wherein the composition is orally administered to the patient.

* * * * *